(12) United States Patent
Mailander et al.

(10) Patent No.: US 8,834,559 B2
(45) Date of Patent: Sep. 16, 2014

(54) STENT

(75) Inventors: Werner Mailander, Birkenfeld (DE); Erik Flaxmeier, Karlsbad (DE); Ralph Steiner, Pforzheim (DE); Frank Scherrible, Kampfelbach (DE)

(73) Assignee: Admedes Schuessler GmbH, Pforzheim (DE)

( * ) Notice: Subject to any disclaimer, the term of this patent is extended or adjusted under 35 U.S.C. 154(b) by 749 days.

(21) Appl. No.: 11/365,470

(22) Filed: Feb. 28, 2006

(65) Prior Publication Data
US 2006/0217799 A1 Sep. 28, 2006

(30) Foreign Application Priority Data
Mar. 23, 2005 (DE) .......................... 10 2005 013 547

(51) Int. Cl.
*A61F 2/06* (2013.01)
(52) U.S. Cl.
USPC ....................................................... 623/1.34
(58) Field of Classification Search
USPC ........... 623/1.13, 1.16, 1.27, 1.34, 1.44, 1.45, 623/1.46, 900, 901, 902, 903, 1.18, 1.19
See application file for complete search history.

(56) References Cited

U.S. PATENT DOCUMENTS

| 5,443,500 | A | 8/1995 | Sigwart |
| 5,632,771 | A | 5/1997 | Boatman et al. |
| 5,741,327 | A | 4/1998 | Frantzen |
| 5,824,054 | A | * 10/1998 | Khosravi et al. ............. 623/1.44 |
| 5,861,027 | A | 1/1999 | Trapp |
| 6,022,374 | A | 2/2000 | Imran |
| 6,231,598 | B1 | 5/2001 | Berry et al. |
| 6,293,966 | B1 | 9/2001 | Frantzen |
| 6,334,871 | B1 | 1/2002 | Dor et al. |
| 6,402,777 | B1 | 6/2002 | Globerman et al. |
| 6,409,752 | B1 | 6/2002 | Boatman et al. |
| 6,464,720 | B2 | 10/2002 | Boatman et al. |
| 6,730,116 | B1 | 5/2004 | Wolinsky et al. |
| 6,863,685 | B2 | 3/2005 | Davila et al. |
| 6,918,928 | B2 | 7/2005 | Wolinsky et al. |
| 2002/0193867 | A1 * | 12/2002 | Gladdish et al. ............. 623/1.15 |

(Continued)

FOREIGN PATENT DOCUMENTS

DE 100 64 596 A1 12/2000
DE 102 35 868 A1 7/2002

(Continued)

OTHER PUBLICATIONS

Schumacher, M., "Diagnostic Workup in Cerebral Aneurysms," *Cerebral Aneurysms*, pp. 13-24, Nakstadt PHj (ed), Bologna, Centauro (2000).

*Primary Examiner* — David Isabella
*Assistant Examiner* — Ann Schillinger
(74) *Attorney, Agent, or Firm* — Kilpatrick Townsend and Stockton, LLP

(57) ABSTRACT

The present invention relates to an aneurysm stent for implantation into a living body, in particular for treatment of aneurysms, in order to implant the stent in the compressed state in a vessel and expand the stent after positioning it in the vessel, having a grid or mesh structure and at least one membrane (2) or a plurality of membranes (2) for covering at least one or more stent cells (1; 3) in the grid or mesh structure, thereby matching the permeation characteristics of the stent structure to the particular characteristics of the aneurysm.

16 Claims, 8 Drawing Sheets

(56) References Cited

U.S. PATENT DOCUMENTS

| | | |
|---|---|---|
| 2002/0193869 A1 | 12/2002 | Dang |
| 2003/0060872 A1 | 3/2003 | Gomringer et al. |
| 2003/0106218 A1 | 6/2003 | Jalisi et al. |
| 2003/0114912 A1* | 6/2003 | Sequin et al. ............... 623/1.11 |
| 2003/0125799 A1* | 7/2003 | Limon ........................ 623/1.15 |
| 2004/0088038 A1 | 5/2004 | Dehnad et al. |
| 2004/0088039 A1 | 5/2004 | Lee et al. |
| 2004/0236407 A1* | 11/2004 | Fierens et al. ............... 623/1.16 |
| 2005/0060025 A1 | 3/2005 | Mackiewicz et al. |
| 2005/0172471 A1 | 8/2005 | Vietmeier |
| 2005/0256564 A1* | 11/2005 | Yang et al. ................... 623/1.42 |
| 2006/0085059 A1 | 4/2006 | Ehrlinspiel et al. |
| 2006/0217799 A1 | 9/2006 | Mailander et al. |
| 2006/0259129 A1 | 11/2006 | Hegel |
| 2007/0027552 A1* | 2/2007 | Farnsworth et al. ....... 623/23.74 |
| 2007/0043429 A1 | 2/2007 | Hegel |

FOREIGN PATENT DOCUMENTS

| | | |
|---|---|---|
| DE | 103 23 475 A1 | 12/2004 |
| DE | 04 014 789 | 3/2005 |
| EP | 0 737 452 A1 | 10/1996 |
| EP | 0 800 800 A1 | 10/1997 |
| EP | 0 801 933 A1 | 10/1997 |
| EP | 0 938 879 A2 | 9/1999 |
| EP | 0 997 116 A2 | 5/2000 |
| EP | 0 891 166 B1 | 1/2005 |
| EP | 1 523 959 A2 | 4/2005 |
| WO | WO 95/01761 A2 | 1/1995 |
| WO | 98/31304 A1 | 7/1998 |
| WO | WO 99/02092 A1 | 1/1999 |
| WO | WO 99/15108 A2 | 4/1999 |
| WO | WO 02/24247 A1 | 3/2002 |
| WO | WO 03/101343 A1 | 12/2003 |
| WO | WO 2004/002368 A1 | 1/2004 |

\* cited by examiner

STENT

CROSS-REFERENCES TO RELATED APPLICATIONS

The present application claims priority to German Application No. 10-2005-013547.1-43, filed Mar. 23, 2005, which is incorporated herein by reference.

BACKGROUND OF THE INVENTION

The present invention relates to a stent system for implantation into a living body, in particular as an aneurysm stent system or endoprosthesis for intracerebral aneurysms.

Intracerebral aneurysms are the most common cause of non-traumatic subarachnoid hemorrhaging. The incidence is 1% in the general population, and, according to autopsy studies, as high as 9%. From a pathomorphological standpoint, intracerebral aneurysms as a rule are genuine saccular aneurysms, which are usually localized in vascular arborizations (see, for example, Schumacher, M., "Diagnostic workup in cerebral aneurysms" in Nakstadt PHj (ed): "Cerebral Aneurysms," pp. 13-24, Bologna: Centauro (2000)).

EP 0737452 describes a stent having additional interwoven threads to reduce the fluid permeability at a portion of the stent.

WO 99/02092 describes an aneurysm stent having a first and second portion, the second portion having reduced fluid permeability. In this stent, the second portion is located only in a limited region of the periphery, in the vicinity of the aneurysm.

BRIEF SUMMARY OF THE INVENTION

One embodiment of the present invention provides an improved aneurysm stent which is simple to manufacture, is easily implanted, and has good X-ray visibility.

The above is achieved by an aneurysm stent according to claim 1, and a manufacturing process according to claim 15. Preferred exemplary embodiments are stated in the dependent claims.

According to the embodiment of the invention, an aneurysm stent system for intracerebral aneurysms is provided for implantation into a living body, the system having a stent with a membrane provided in at least one stent cell. The membrane reduces or eliminates the blood permeability of the stent cell in the radial direction of the stent, resulting in a region with decreased blood permeability which may be located on or in the region of an aneurysmal neck. In other words, there are stent cells which are coated or covered at least in part by a membrane in order to reduce or eliminate fluid permeability through the stent cell, and there are non-covered stent cells which allow essentially unhindered permeation of a fluid. In this manner, an implanted stent allows a bodily tissue in the vicinity of the periphery of the stent to receive either an unhindered blood supply (for non-covered stent cells), or a reduced blood supply (for covered stent cells), and/or allows the blood circulation in an aneurysm to be greatly modified, turbulently intermixed, or minimized. In this manner the circulatory characteristics in the aneurysm are modified.

The modified blood permeability (resulting from the positioning of the membrane or multiple membranes) influences the flow through the stent structure in the radial direction of the stent such that a mass flow rate into the aneurysm is limited. This limitation of the flow rate results in thrombogenesis of the blood in the aneurysm, and thus to obliteration of the aneurysm.

The entire stent system is compressible to allow it to be inserted into an insertion system. The stent system is preferably self-expanding so that the system automatically expands when taken out of the insertion system.

The aneurysm stent is implanted into a living body, in particular for treatment of aneurysms, and has a substantially tubular shape which allows the stent to be implanted in the collapsed or compressed state into the living body.

Thrombogenesis is enhanced, and rupture of the aneurysm is prevented, by providing multiple membranes in a uniform row so that the stent has lower fluid permeability in a specified region. Rotation of the inserted stent is unnecessary, since the specified region with reduced fluid permeability may be situated over the entire periphery of the stent.

The membrane preferably includes an X-ray-visible material such as platinum, $BaSO_4$, platinum-iridium, gold, or tantalum, for example.

The aneurysm stent is implanted in the compressed state in a vessel in a living body, in particular for treating aneurysms, and is expanded after being positioned in the vessel. The stent has a grid or mesh structure, and has at least one membrane or a plurality of membranes for covering at least one or more stent cells in the grid or mesh structure.

The membrane is preferably provided in the cross section of the covered stent cell within the web thickness of the stent cell, so that the membrane does not project from the stent structure. This allows a reliable insertion of the stent into a vessel without damage or slippage of the membrane.

The membrane preferably is less thick than the web thickness of the stent cell, so that the membrane is fully enclosed and protected by the webs of the stent cells.

However, the membrane may also have essentially the same thickness as the web thickness of the stent cell if a particularly thick membrane is desired.

The membrane preferably includes a polymer, preferably a thermoplastic elastomer, and is attached to the webs of the stent cell by adhesion.

The membrane preferably includes an X-ray-visible material to allow monitoring of the position of the implanted stent and the membrane.

The membrane may also be filled with a medication which is successively dispensed into the body after the implantation.

The membrane may have a porous structure or a closed structure for matching the permeation characteristics of the stent. A plurality of stent cells in a uniform row is preferably covered by a membrane. In this regard, an open stent cell may follow a stent cell that is covered by the membrane. Porous as well as closed membranes may be provided to optimize matching of the permeation characteristics to the particular circumstances.

In the method according to the invention, a stent structure is provided having webs as well as stent cells formed between the webs, and a membrane is applied to the webs of at least one stent cell. The membrane preferably is applied to the webs by adhesion.

The membrane may also be filled with a medication or an X-ray-visible material.

The aneurysm stent according to the invention is preferably used as a balloon-expanded aneurysm stent.

BRIEF DESCRIPTION OF THE DRAWINGS

The invention is explained in greater detail below based on preferred exemplary embodiments, with reference to the drawings, which show the following.

DETAILED DESCRIPTION OF THE INVENTION

Figure 1:
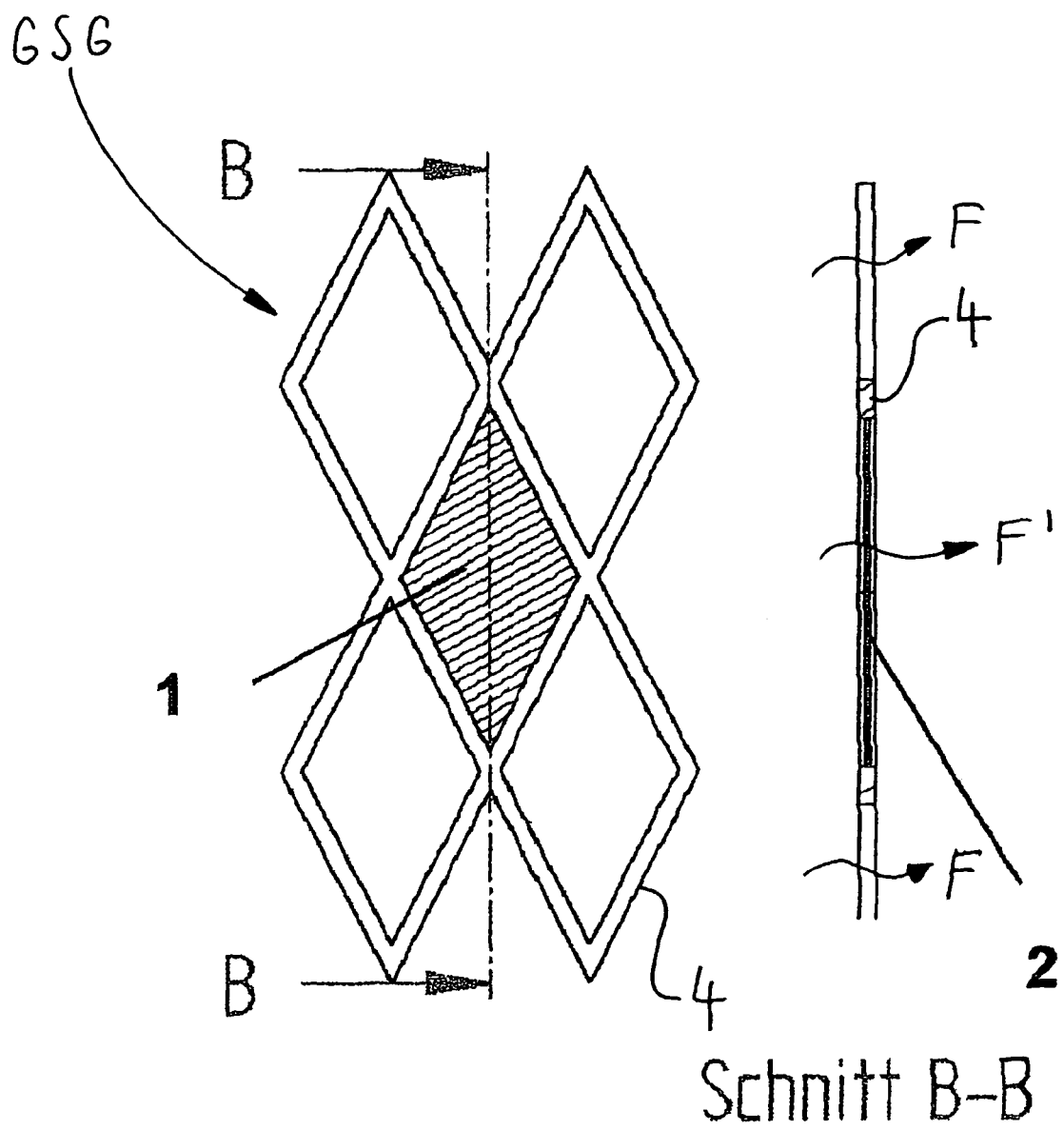
FIG. 1 shows a first exemplary embodiment of an aneurysm stent according to the invention having a closed stent cell.
Figure 2:
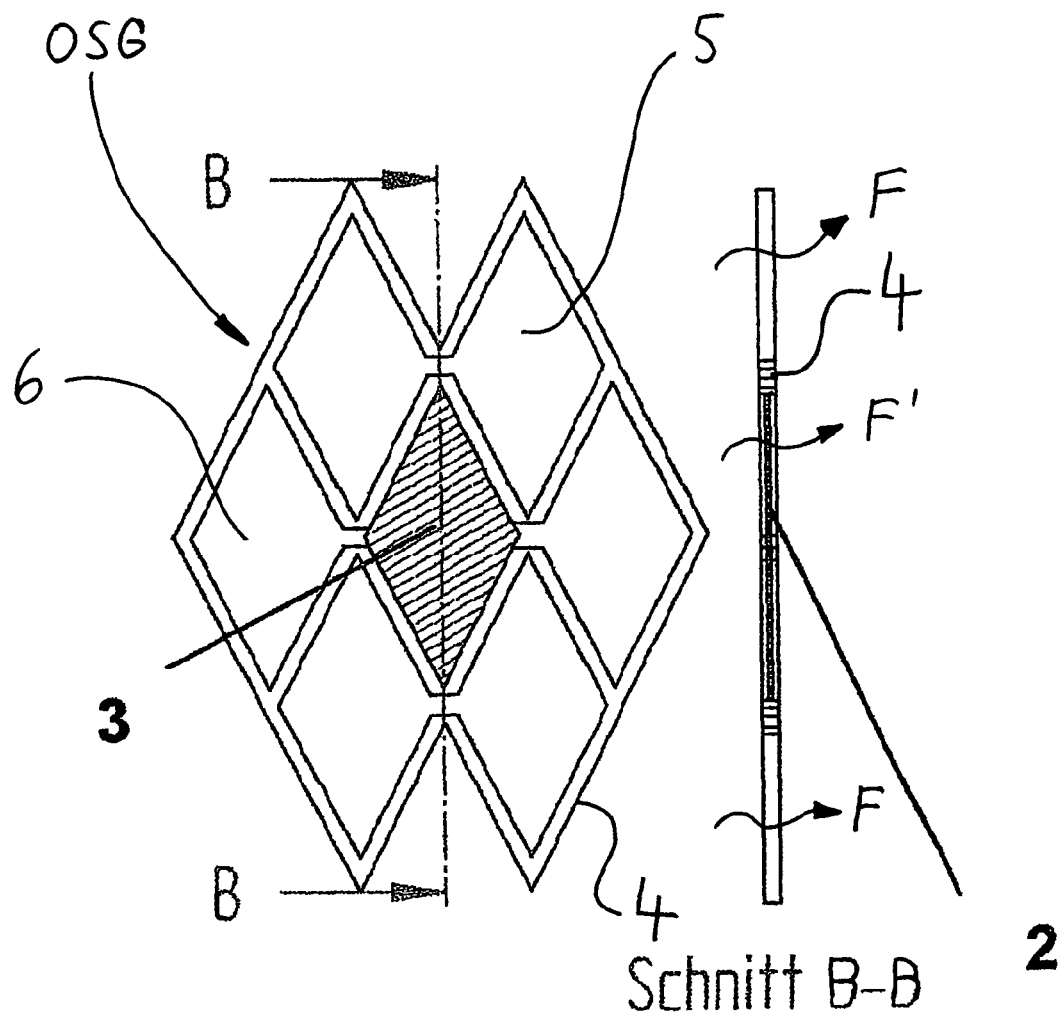
FIG. 2 shows a second exemplary embodiment of an aneurysm stent according to the invention having an open stent cell.

As shown in FIGS. 1 and 2, an aneurysm stent according to the invention has a covered stent cell 1, 3 which is at least partially covered by a membrane 2 by the fact that the membrane 2 is inserted into the stent cell 1, 3 and is attached to the webs 4 of the cell 1, 3. The configuration of the membrane 2 to form a partially covered stent is possible for a stent having a closed stent cell geometry CSG, as shown in FIG. 1, as well as for a stent having an open stent cell geometry OSG, as shown in FIG. 2. The open stent cell geometry OSG may have two, three, or more stent cells 3. FIG. 2 shows an open stent cell geometry OSG having two connected stent cells, i.e., open stent cells 5 and an open stent cell geometry OSG, with three connected stent cells 6.

The stent has essentially unhindered fluid permeability in the radial direction through its non-covered stent cells, as indicated by F in FIGS. 1 and 2, and has reduced, eliminated, or interrupted fluid permeability in the vicinity of the stent cells 1, 3 covered by a membrane, as indicated by F' in FIGS. 1 and 2.

The membrane 2 includes a flexible material to compensate for dimensional changes of the stent during contraction and expansion. For example, the membrane 2 is produced from a polymer, preferably a thermoplastic elastomer such as TPE-U, TPE-A, TPE-E, TPE-S, TPE-V, PU, EVA, or silicone and compounds thereof. The membrane 2 preferably is attached to the webs 4 of the stent structure by adhesion.

The membrane 2 preferably is less thick than the web thickness of the stent structure, as shown in sections B-B of FIGS. 1 and 2, so that the membrane 2 does not project from the stent structure. However, the membrane 2 may also have a greater thickness, up to the web thickness.

For implantation, the stent is loaded into an insertion system, such as a catheter, and after positioning in the affected vessel the stent is expanded. The expansion is achieved by inflating a balloon and/or by the shape memory characteristics of the stent structure.

The stent structure preferably has a geometry corresponding to Application DE 10 2004 012 837.5, DE 102 28 529.2 (PCT/EP03/06775), or DE 103 23 475.6, which are incorporated by reference. The stent structure preferably is expanded in such a way that it preferentially lies flat against a wall of the blood vessel and supports same. The membranes 2 are situated so that reduced permeation results through the stent structure in the vicinity of an aneurysm neck, or the aneurysm neck is covered. Thus, a reduced blood flow can be provided only into the aneurysm, and the blood circulation in the aneurysm is modified, i.e., the blood is turbulently intermixed and/or the blood permeation is reduced, thereby enhancing thrombogenesis and preventing rupture of the aneurysm.

It is particularly advantageous for the described stent to be produced from stainless steel or a cobalt-chromium-tantalum alloy. Thus, the stent is preferably expanded in the body by use of an expansion device such as a balloon catheter. The invention or a preferred embodiment thereof is preferably implemented using a balloon-expanded stent made of stainless steel, tantalum, niobium, and cobalt alloys. It is also possible to use stents made of other materials, such as polymers, self-disintegrating materials (e.g., lactic acid materials or derivatives), and stents made of nitinol (nickel-titanium alloys) and/or other self-expanding materials, or (preferably temperature-dependent) shape memory materials (i.e., materials with a shape memory effect).

The membrane 2 is preferably filled with an X-ray-visible material such as tantalum, platinum, $BaSO_4$, platinum-iridium, or gold, for example. The membrane 2 may also be provided with a medication filling to successively supply the body with medications. For a row of membranes, as shown in FIGS. 3 through 8, it is possible to fill only individual membranes 2 with X-ray-visible material and to fill other membranes 2 with a medication, while other membranes have no filling.

Figure 3:
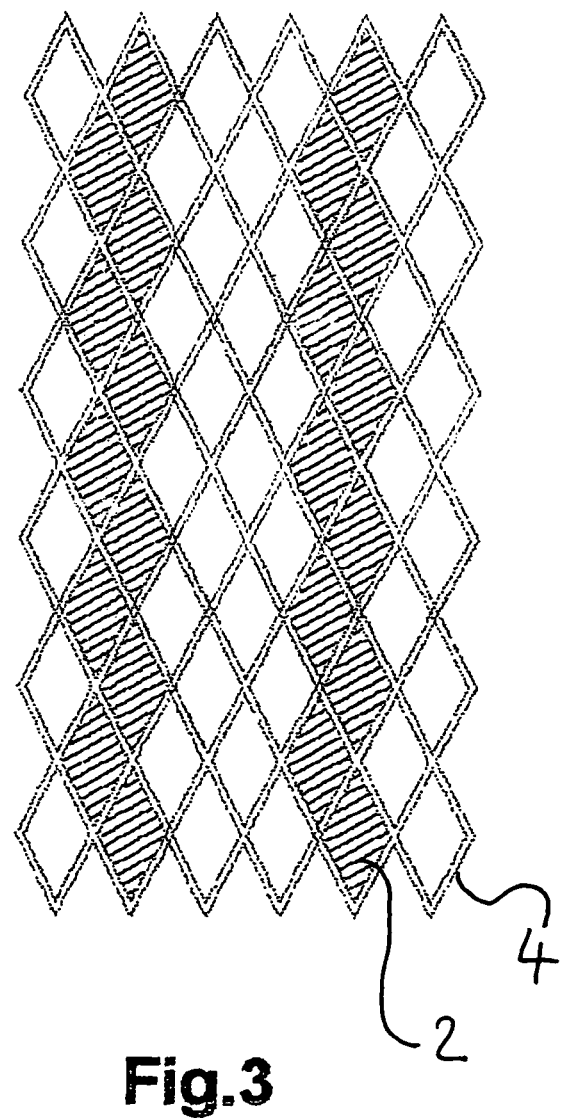
FIG. 3 shows an aneurysm stent according to the invention in which adjacent stent cells in the axial direction are covered by a membrane.
Figure 4:
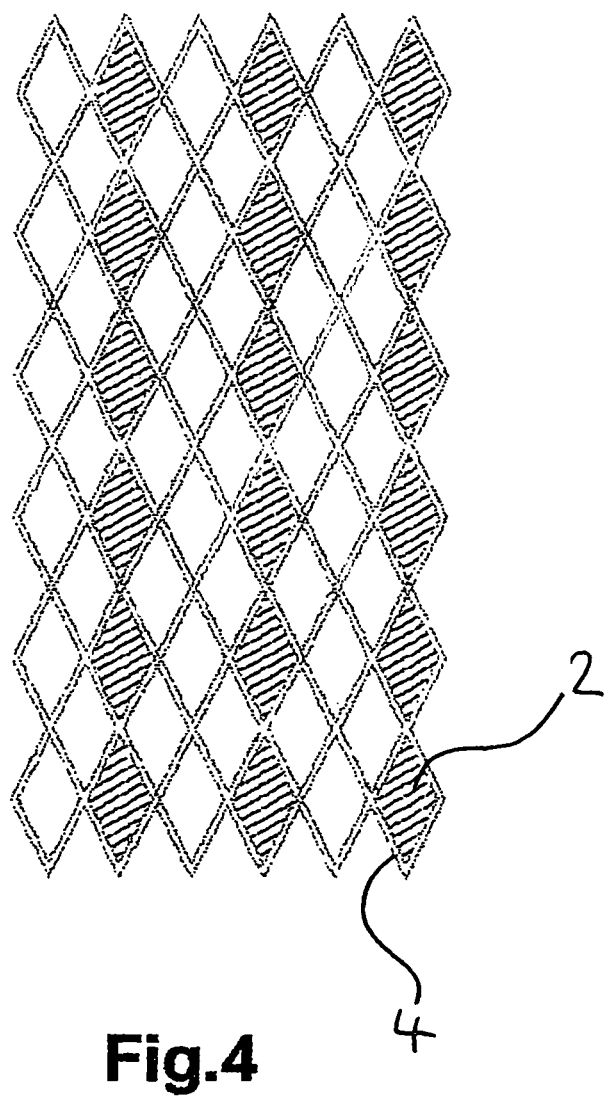
FIG. 4 shows another aneurysm stent according to the invention in which adjacent stent cells in the axial direction are covered by a membrane.
Figure 5:
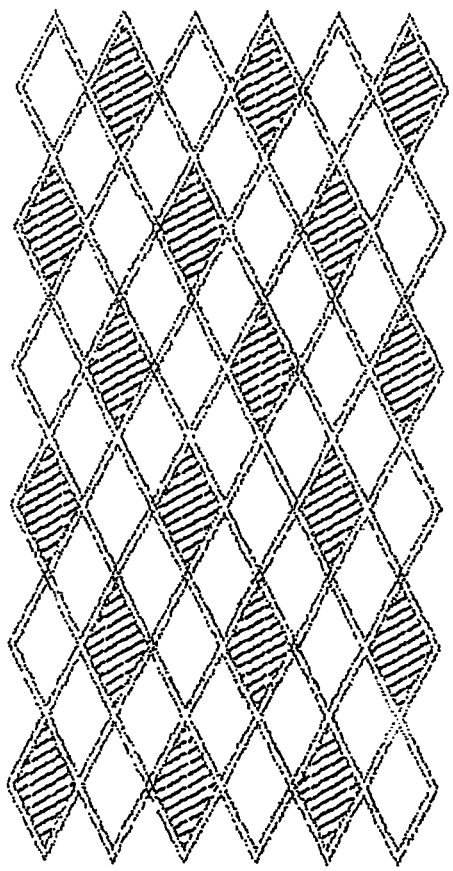
FIG. 5 shows a further aneurysm stent according to the invention in which a stent cell covered by a membrane is alternated with an open stent cell in the axial direction.
Figure 6:
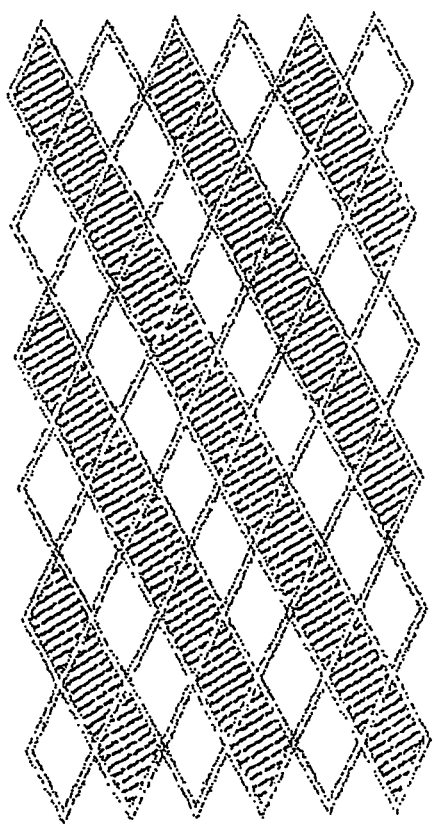
FIG. 6 shows a further aneurysm stent according to the invention in which multiple rows of adjacent stent cells are covered by a membrane, the rows being spirally configured.
Figure 7:
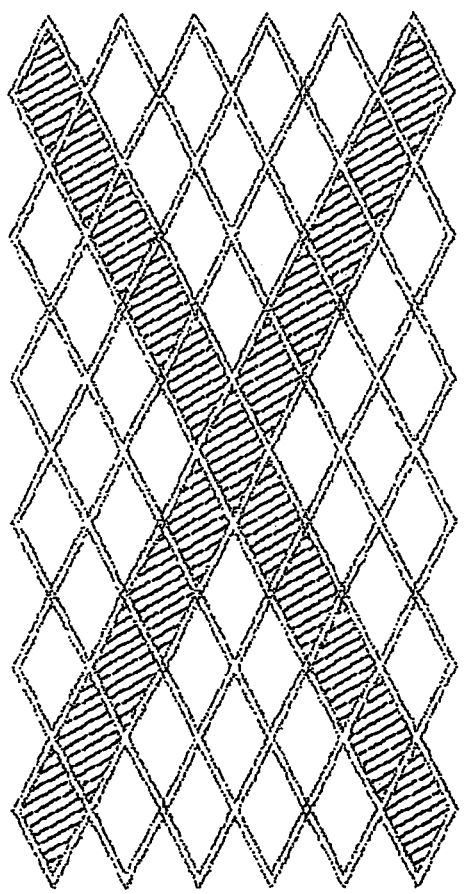
FIG. 7 shows a further aneurysm stent according to the invention in which two spirally configured rows having stent cells covered by a membrane are configured in a cross shape in the projection.
Figure 8:
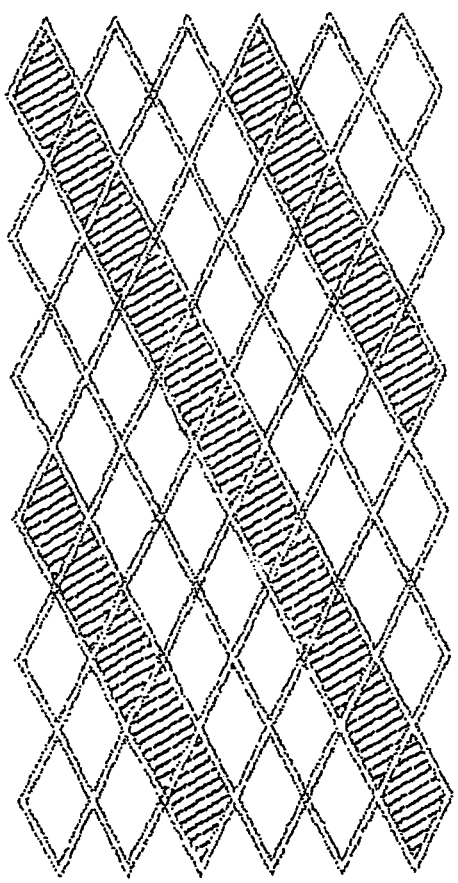
FIG. 8 shows a further aneurysm stent according to the invention, similar to that shown in FIG. 6, in which multiple rows on adjacent stent cells are covered by a membrane, the rows being spirally configured and, in contrast to the stent shown in FIG. 6, every two open rows are situated between the covered rows.

To match the permeability characteristics to the particular conditions, open, i.e., non-covered, stent cells 1, 3 are alternated with stent cells 1, 3 covered by the membranes 2. In this manner the covered stent cells 1, 3 adjacent to one another may be configured in an axial row, as shown in FIG. 3 or 4, or an open stent cell 1, 3 is alternated with a covered stent cell 1, 3, as shown in FIG. 5, or the covered stent cells 1, 3 are configured in one or more spiral rows, as shown in FIGS. 6 through 8.

Furthermore, the permeation characteristics may be modified by the membrane structure used. A closed membrane structure may be used to completely eliminate permeation through the stent cell 1,3, or a porous membrane structure may be used to merely reduce but not completely eliminate the permeation. Alternatively, the permeation may be reduced by use of an open membrane structure or a membrane 2 which only partially covers a stent cell 1, 3. Both types of membrane 2, closed and porous/open, may be provided within a stent.

The membrane 2 is also designed in such a way that it is tightened or slightly stretched by the expansion of the stent. In other words, for a compressed stent the membrane 2 is provided in a corrugated or slightly curved state inside the stent cell 1, 3, and is drawn out essentially straight or flat by the expansion of the stent.

A reduced fluid permeability or blood permeability results in the region of the membrane 2. During implantation, this region is situated in the vicinity of the aneurysm to achieve the desired effect of reduced blood permeability. Since the region of reduced permeability may be provided in the overall peripheral region of the stent, it is not necessary to rotate the inserted stent to provide the region with reduced blood permeability for the aneurysm, with the result that the circulation characteristics of the blood in the aneurysm are modified, turbulently intermixed, or reduced. This simplifies the insertion operation and reduces the risk of injury.

The exemplary embodiments shown may be implemented in any given combination. For example, a stent may have both open stent cells 3 and closed stent cells 1. Furthermore, the configuration of the rows of covered stent cells is not limited to those shown here, but, rather, may be configured in any given pattern, depending on the application. The stent cells may also have a different shape than the diamond shape shown here.

The described stents may be provided, at least in places, with a thrombogenic coating of, for example, platinum or another metal or pharmaceutical. The stent may also be designed as a drug-eluding stent. Furthermore, the stent may be advantageously used to prevent collapse of the vessel or cavity and support the wall(s). The described stent may be cut, milled, or bored from a tubular raw material, or may have a flat shape and be subsequently provided with a tubular shape.

What is claimed is:

1. An aneurysm stent for implantation into a living body for the treatment of aneurysms, the stent comprising:
   a compressed state for positioning the stent in a vessel and an expanded state for treating the aneurysm, the aneurysm stent having a grid or mesh structure comprising non-covered stent cells and covered stent cells, wherein the stent cells are compressed when the stent is in the compressed state, wherein each covered stent cell contains a membrane, the membrane having a non-porous or closed structure to reduce fluid permeability in a region of the membrane, and wherein each entire membrane is provided in the corresponding covered stent cell within a thickness of that stent cell so that each membrane does not project beyond a thickness of the grid or mesh structure.

2. An aneurysm stent according to claim 1, wherein the membrane is less thick than the web thickness of the corresponding covered stent cell.

3. An aneurysm stent according to claim 1, wherein the membrane has essentially the same thickness as the web thickness of the corresponding covered stent cell.

4. An aneurysm stent according to claim 1, wherein the membrane includes a polymer.

5. An aneurysm stent according to claim 1, wherein the membrane is attached to webs of the corresponding covered stent cell by adhesion.

6. An aneurysm stent according to claim 1, wherein the membrane includes an X-ray-visible material.

7. An aneurysm stent according to claim 1, wherein the membrane is filled with a medication.

8. An aneurysm stent according to claim 1, wherein a plurality of stent cells in a uniform row or in a uniform pattern is covered by the membrane.

9. An aneurysm stent according to claim 1, wherein at least one covered stent cell is positioned adjacent to a non-covered stent cell.

10. An aneurysm stent according to claim 1, wherein a plurality of the non-covered stent cells are interconnected.

11. An aneurysm stent according to claim 1, wherein the stent structure has a tubular shape.

12. A method for producing an aneurysm stent, the method comprising:
    preparing a stent structure from a material having shape memory characteristics with webs, the stent structure having first and second stent cells formed between the webs, the stent structure compressible into a compressed state in which the stent cells are compressed; and
    in each of the first stent cells, attaching a membrane to the webs of the first stent cell such that the second stent cells are not covered by the membrane, each membrane having a non-porous or closed structure to reduce fluid permeability in a region of the membrane, and wherein each entire membrane is provided in the corresponding first stent cell within a web thickness of the corresponding first stent cell so that the membrane does not project beyond the stent structure.

13. A method according to claim 12, wherein the membrane is attached to the webs by adhesion.

14. A method according to claim 12, wherein the membrane is filled with a medication.

15. A method according to claim 12, wherein the membrane is provided with an X-ray-visible material.

16. A method according to claim 12, wherein the stent structure has a tubular shape.

* * * * *